United States Patent [19]
Sholder

[11] Patent Number: 5,690,689
[45] Date of Patent: *Nov. 25, 1997

[54] DUAL-CHAMBER IMPLANTABLE STIMULATION DEVICE HAVING ADAPTIVE AV INTERVALL AND METHOD FOR TREATING CARDIOMYOPATHY THEREOF

[75] Inventor: Jason A. Sholder, Beverly Hills, Calif.

[73] Assignee: Pacesetter, Inc., Sylmar, Calif.

[*] Notice: The term of this patent shall not extend beyond the expiration date of Pat. No. 5,340,361.

[21] Appl. No.: 625,023

[22] Filed: Mar. 29, 1996

Related U.S. Application Data

[63] Continuation-in-part of Ser. No. 224,439, Apr. 8, 1994, abandoned, which is a continuation-in-part of Ser. No. 975,747, Nov. 13, 1992, Pat. No. 5,340,361.

[51] Int. Cl.$^6$ ................................................. A61N 1/36
[52] U.S. Cl. .................................................. 607/24
[58] Field of Search ................................... 607/24, 9

[56] References Cited

U.S. PATENT DOCUMENTS

4,554,921  11/1985  Nappholz et al.
5,340,361  8/1994  Sholder ..................................... 607/24

Primary Examiner—Scott M. Getzow

[57] ABSTRACT

A dual-chamber implantable pacemaker configured to operate in the DDD or DDDR mode automatically sets its AV (or PV) interval to an amount that is equal to the natural conduction time of a patient plus or minus a small prescribed amount, e.g., 1–100 msec. When set to a value that is less than the natural conduction time, preemptive ventricular pacing thus occurs at a time in the patient's cardiac cycle that is near when a natural ventricular contraction (an R-wave) would occur. Such ventricular pacing causes a mechanical contraction sequence of the patient's heart that differs from the natural contraction sequence following a natural depolarization, resulting in improved cardiac output. The pacemaker includes a pulse generator that generates ventricular stimulation pulses (V-pulses) at the conclusion of a pacemaker-defined AV (or PV) interval if no natural ventricular activity (an R-wave) is sensed during such AV (or PV) interval. The AV (or PV) intervals are automatically adjusted by the pacemaker to be a function of the natural conduction time sensed by the pacemaker, where the natural conduction time is the time between atrial activity (a sensed P-wave or a delivered A-pulse) and the subsequent natural ventricular activity (R-wave).

20 Claims, 6 Drawing Sheets

DUAL-CHAMBER IMPLANTABLE STIMULATION DEVICE HAVING ADAPTIVE AV INTERVALL AND METHOD FOR TREATING CARDIOMYOPATHY THEREOF

CROSS REFERENCE

This application is a continuation-in-part of application Ser. No. 08/224,439, filed Apr. 8, 1994, abandoned, which is a continuation-in-part of application Ser. No. 07/975,747, filed Nov. 13, 1992, now U.S. Pat. No. 5,340,361.

FIELD OF THE INVENTION

The present invention relates to implantable medical devices and methods, and more particularly to an implantable pacemaker that automatically adapts its atrial-ventricular (AV) delay to a value determined from the measured natural conduction time of a patient. Such pacemaker is particularly suited for maximizing the cardiac output of patients suffering from cardiomyopathy.

BACKGROUND OF THE INVENTION

The heart is a pump that pumps life-sustaining blood throughout the body of the patient. The human heart comprises a left side and a right side, with each side having a first chamber, known as the atrium, and a second chamber, known as the ventricle. The atrium receives blood returning from other body locations. At an appropriate time, determined by the sinoatrial (SA) node, an electrical stimulus is provided that causes the muscle tissue surrounding the atrium to depolarize. Depolarization of the atrial muscle tissue is manifest by the occurrence of an electrical signal known as the P-wave. Immediately following the P-wave, the atrial muscle tissue physically (mechanically) contracts, forcing the blood held in the atrium through a one-way valve into the ventricle. The SA node stimulus that caused the atrium to depolarize also travels to the ventricle through the atrioventricular (AV) node and the atrioventricular (AV) bundle. The AV node is a mass of modified heart muscle situated in the lower middle part of the right atrium. It receives the impulse to contract from the sinoatrial node, via the atria, and transmits it through the atrioventricular bundle to the ventricles. The AV bundle is a bundle of modified heart muscle fibers (Purkinje fibers) that pass from the AV node forward to the septum between the ventricles, where it divides into right and left bundles, one for each ventricle. The fibers thus transmit the SA node stimulus from the atria, via the AV node, to the ventricles. However, as the SA node stimulus travels through the AV bundle, it is delayed by an amount commensurate with the same time it takes the blood to physically flow from the atrium to the ventricle.

After the delay through the AV bundle, which delay may be referred to as the natural conduction time of the heart, the stimulus arrives at the ventricular muscle tissue, causing it to depolarize. Depolarization of the ventricular muscle tissue is manifest by the occurrence of an electrical signal known as the R-wave. Immediately following the R-wave, the ventricular muscle tissue physically contracts, forcing the blood held therein through one or more arteries to various body locations. In this manner, then, the heart "beats" or pumps blood, by having the atria contract, at a rate determined by the SA node and, after a short delay, by having the ventricles contract. After a longer delay, when the atrium has refilled with blood returning from throughout the body, the process repeats.

The heart of a typical healthy patient may beat 60–70 times per minute when the patient is at rest. When the patient is undergoing significant physiological stress, as occurs, e.g., during physical exercise, the heart rate increases significantly (e.g., up to 150–170 times per minute). The above-described process wherein the atria and ventricles sequentially depolarize and contract in order to pump blood, and get ready to depolarize again, is known as the "cardiac cycle." The length of the cardiac cycle (which represents the period of the heart rate) may be measured as the time interval between successive P-waves or R-waves, although R-waves are usually used because they are easier to detect.

A pacemaker is an implantable medical device that monitors the activity of the heart for the occurrence of P-waves and/or R-waves, and steps in with electronically-generated stimuli, when needed, to force the depolarization of the atria and/or ventricles. A pacemaker-generated stimulus that is delivered to the atrium is referred to herein as an "A-pulse." A pacemaker-generated stimulus that is delivered to the ventricle is referred to herein as a "V-pulse." Most pacemakers are configured to provide an A-pulse and/or a V-pulse only if a prescribed period of time has elapsed without the occurrence of a P-wave and/or an R-wave, i.e., without the occurrence of natural heartbeats.

The prescribed period of time used by the pacemaker between contraction of the ventricle and contraction of the atrium is generally referred to as the V-A Interval, or the atrial escape interval. For most dual-chamber pacemaker modes of operation, only if a P-wave does not occur during the atrial escape interval will the pacemaker step in at the conclusion of such interval and generate an A-pulse.

The prescribed period of time used by the pacemaker between contraction of the atrium and contraction of the ventricle is referred to as the A-V Interval, or sometimes it is called the "AV Delay." The pacemaker, for most dual-chamber modes of operation, generates a V-pulse only if the AV Delay elapses without the occurrence of an R-wave.

In the above-described manner, the heart is thus afforded as much time as possible to beat on its own before the electronically-generated stimuli of the pacemaker are delivered to the heart, causing it to beat at the rate set by the pacemaker.

Heretofore, most cardiac patients using a pacemaker have suffered from at least one of various cardiac conditions or diseases that affect either the ability of the SA node to maintain and sustain a satisfactory heartbeat rate (hereafter "rate problems"), or the ability of the AV node or the AV bundle to conduct a suitable stimulus to the ventricle (hereafter "conduction problems"). Advantageously, both rate problems and conduction problems lend themselves well to a pacemaker solution because the underlying cardiac muscle tissue is in place and is capable of responding to the electronically-generated stimuli produced by the pacemaker.

Unfortunately, there remain a significant number of patients that suffer from one or more conditions that cannot be characterized as either rate problems or conduction problems. One such problem is known as hypertrophic obstructive cardiomyopathy (HOCM). Another is known as dilated cardiomyopathy (DCM). While there are medical or clinical differences between these two forms of cardiomyopathy, for purposes of the present invention they may be considered the same problem, and will be referred to hereafter as simply "cardiomyopathy."

In general, a patient suffering from cardiomyopathy experiences a significant reduction in cardiac output because the heart muscle is either weakened (e.g., in a dilated cardiomyopathy), or thickened (e.g., in a hypertrophic obstructive cardiomyopathy) and this thickening can cause an obstruction to blood flow. Thus, a patient suffering from cardiomyopathy will generally have reduced blood flow per heartbeat (stroke volume) as may be needed.

Cardiomyopathy patients are referred to as being moderately to severely symptomatic of low cardiac output syndrome. The treatment for low cardiac output syndrome, up to now, has been certain drugs and/or heart transplantation. Drug therapy rarely works and, disadvantageously, heart transplantation is not a viable solution for most patients. Not only are hearts suitable for transplant difficult and expensive to secure, but even when secured, a very dangerous and complicated surgery must follow in order to successfully perform the transplantation operation. What is thus needed is an alternative to heart transplantation for patients suffering from low cardiac output syndrome.

In accordance with the present invention, a dual-chamber pacemaker is implanted in patients suffering from low cardiac output syndrome and is configured to provide PV or AV pacing. During PV or AV pacing, the pacemaker delivers a V-pulse to the ventricles a programmed delay after the occurrence of an atrial event, which atrial event could be either the occurrence of a P-wave or the delivery of an A-pulse.

Advantageously, by forcing a ventricular contraction prior to the occurrence of an R-wave, the cardiac output of patients suffering from cardiomyopathy may be significantly improved. Such improvement appears to result because the ventricular stimulus—a V-pulse delivered by the pacemaker—is applied to the ventricular tissue at a different cardiac location (at the location of the ventricular lead tip electrode, which location is usually in the apex of the right ventricle) than is the natural stimulus when received through the natural conduction system.

For example, stimulation by the natural conduction system in a patient suffering from hypertrophic obstructive cardiomyopathy results in muscle tissue contracting in an obstructive manner, which can prevent blood from being ejected from the ventricle. The obstruction can take the form of a narrowing of the ventricular chamber due to an enlarged septum and/or wall tissue. The left ventricular outflow tract may be further obstructed, when stimulated by the natural conduction system, by the systolic motion of the mitral valve against the hypertrophied septum. In these patients, stimulation from the apex results in a different physical or mechanical contraction sequence of the cardiac muscle tissue than occurs from a natural stimulus received through the natural conduction system. Upon delivery of the V-pulse, the cardiac muscle tissue mechanically contacts in a somewhat different sequence (i.e., from the apex and upward), resulting in altered squeezing forces to pump the blood. Such different mechanical contraction sequence, for many cardiomyopathy patients, advantageously results in an increased cardiac output.

For patients suffering from dilated cardiomyopathy, the stimulation site and sequence of activation which provides the best mechanical contraction is still controversial. However, at this time, it is believed that these patients may also benefit from a stimulation site other than the natural conduction system.

PV or AV pacing is only effective, however, when the V-pulse is delivered to the ventricular tissue before the occurrence of an R-wave, i.e., before the ventricular tissue depolarizes. It is thus necessary, if AV or PV pacing is to be used, to set the AV (or PV) interval of the pacemaker to a value that is less than the patient's normal conduction time. Unfortunately, heretofore, this requirement has forced the AV (or PV) interval to be set to very short values, i.e., between 80 and 120 msec, because during exercise (or other periods of physical activity or physiological stress) the patient's native conduction time may shorten significantly. Thus, in order to guarantee that the pacemaker will always pace the ventricles, i.e., in order to assure that the V-pulse is delivered to the ventricular tissue at a time that precedes a normal R-wave, the AV (or PV) interval must be set to an interval that is shorter than any native conduction interval that might exist in any given patient at any given time.

Disadvantageously, setting a very short programmed AV (or PV) interval may adversely affect cardiac output because it may force ventricular contraction well before the ventricles have had sufficient time to be filled with blood from the atrium. Thus, what is needed for patients suffering from cardiomyopathy is a pacemaker that paces the ventricles at a time in the cardiac cycle that is always less than the natural conduction time, i.e., at a time that is prior to the occurrence of an R-wave, but that is not so much less than the natural conduction time so as to adversely affect cardiac output. That is, what is needed is a pacemaker that automatically sets its internally-generated AV and/or PV intervals to be just short of the patient's native conduction time, thereby assuring that the AV (or PV) interval is sufficiently long to allow the blood to physically move from the atrium to the ventricles; yet remains sufficiently short to always be less than the patient's native conduction time.

When the AV and/or PV interval is shortened to a value that is just less than the native conduction time, there is also a need to regularly check the set interval to determine whether it is still set at a value that is less than the patient's native conduction time. This is because the patient's native conduction time will normally change over a period of time. A particular stair-step searching technique for regularly checking the AV and/or PV interval to determine if it is still less than the native conduction time is described in commonly-assigned U.S. Pat. No. 5,334,220, issued Aug. 2, 1994, entitled "Dual-Chamber Implantable Pacemaker Having An Adaptive AV Interval that Prevents Ventricular Fusion Beats and Method of Operating Same," which patent is incorporated herein by reference. Another technique for setting the AV and/or PV interval so that it differs from the natural or native conduction time by an amount Δ is described in applicant's copending patent application Ser. No. 08/440,599, filed May 15, 1995, entitled "Dual-Chamber Implantable Pacemaker Having its AV Interval Automatically Set as a Function of a Measured Natural Conduction Time," which application is also incorporated herein by reference. It would also be desirable to employ other techniques or systems wherein the AV or PV interval is always maintained at an interval that bears a prescribed relationship to the patient's natural conduction time, thereby obviating the need to periodically "search" for such an optimum value.

The present invention advantageously addresses the above and other needs.

SUMMARY OF THE INVENTION

The present invention is directed to a dual-chamber pacemaker that adaptively adjusts its AV interval to assure that it remains a fixed amount less than or more than the measured natural conduction time of a patient.

In accordance with one aspect of the invention, the AV interval of the pacemaker is set to a fixed amount less than the measured natural conduction time. The pacemaker is then used to provide a method of treating a patient suffering from cardiomyopathy through preemptive ventricular pacing.

More particularly, in accordance with such aspect of the invention, a dual-chamber pacemaker, and a method of operating such a dual-chamber pacemaker, wherein the natural conduction time of a patient is measured, and the AV (or PV) interval of the pacemaker is automatically set to a value that is a prescribed function of the measured natural conduction time, e.g., x milliseconds less than the natural conduction time. A ventricular stimulation pulse (V-pulse) is then generated at the conclusion of the pacemaker-defined AV (or PV) interval in advance of a spontaneous R-wave. Such V-pulse is thus applied to the ventricular muscle tissue at a time when such muscle tissue is capable of responding thereto, i.e., at a time when the tissue is not refractory. As such, the V-pulse (absent a decreasing natural conduction time) preempts the R-wave, and initiates a mechanical contraction sequence that is different from the mechanical contraction sequence following an R-wave. For many patients suffering from cardiomyopathy, such different mechanical contraction sequence advantageously increases their cardiac output. In the event that an R-wave consistently occurs, signaling that the natural conduction time of the patient may be decreasing (as might occur, for example, if the patient is exercising), the consistent occurrence of the R-wave provides a new measure of the natural conduction time, which thereafter affords a basis for further adjustment of the AV interval.

In accordance with another aspect of the invention, the AV or PV interval of the dual-chamber implantable pacemaker may be automatically set to a value that is a prescribed amount greater than a measured natural conduction time.

The pacemaker-defined AV interval begins upon the delivery of an atrial stimulation pulse (A-pulse) by the pacemaker. Similarly, the pacemaker-defined PV interval begins upon sensing natural atrial activity (a P-wave) by the pacemaker. The natural conduction time measured by the pacemaker comprises the time between atrial activity (whether a sensed P-wave or a delivered A-pulse, whichever occurs) and subsequent natural ventricular activity (an R-wave).

A method of operating a pacemaker in accordance with the present invention includes: (1) measuring the natural conduction time, $t_{AR}$, of the patient in a given cardiac cycle; and (2) setting the AV (or PV) interval of the pacemaker, for use in subsequent cardiac cycles, to a value that is equal to $t_{AR}$, plus or minus a prescribed amount, e.g., 1–100 msec. For treating cardiomyopathy, the AV (or PV) interval will be set to a value that is less than $t_{AR}$. For other purposes, the AV (or PV) interval may be set to a value that is greater than $t_{AR}$. In either event, the AV (or PV) interval is always set to a value that is related to the measured value of $t_{AR}$.

In accordance with a further aspect of the invention, the pacemaker includes a timing counter, or equivalent, that is initiated upon the occurrence of each atrial event, whether a P-wave or an A-pulse. The atrial event also starts the AV (or PV) interval of the pacemaker. If an R-wave occurs in the cardiac cycle before the termination of the AV (or PV) interval, then the timing counter stops, with the count held therein providing a measure of the natural conduction time, $t_{AR}$. The AV (or PV) interval set by the pacemaker is then immediately and automatically adjusted to a new value that is the prescribed amount less or greater than $t_{AR}$. The new adjusted value of the AV (or PV) interval is then used for the next cardiac cycle. In this manner, the AV (or PV) interval is adaptively adjusted, as required, to always be less or greater than the natural conduction time of the patient.

It is noted that the measurement of the natural conduction time, $t_{AR}$, is not done for the purpose of adjusting the rate of the pacemaker. Rather, it is done for the purpose of setting the AV (or PV) interval of the pacemaker to a value that will assure a desired type of pacing.

In accordance with yet another aspect of the invention, if a prescribed number of consecutive cardiac cycles ensue without the occurrence of an R-wave, i.e., if preemptive ventricular pacing has occurred for the prescribed number of consecutive cardiac cycles, then a new measurement of the natural conduction time may be made so that the value of the AV (or PV) interval may be adjusted appropriately to remain within a prescribed $\pm\Delta$ amount of the newly measured natural conduction time.

A dual-chamber pacemaker made in accordance with the present invention includes an atrial channel and a ventricular channel. An atrial sense amplifier senses the occurrence of natural atrial activity (a P-wave) in the atrial channel. A ventricular sense amplifier similarly senses the occurrence of natural ventricular activity (an R-wave) in the ventricular channel. An atrial pulse generator generates an atrial stimulation pulse (A-pulse) in the atrial channel in the absence of a sensed P-wave by the atrial sense amplifier within an AV time interval. Similarly, a ventricular pulse generator generates a ventricular stimulation pulse (V-Pulse) in the ventricular channel in the absence of a sensed R-wave by the ventricular sense amplifier within an atrial escape interval. A control system coupled to both the atrial and ventricular channels defines the AV time interval and the atrial escape interval. The AV time interval begins upon the sensing of atrial activity in the atrial channel, where atrial activity may be either a P-wave or the generation of an A-pulse, whichever event occurs. The atrial escape interval begins upon the sensing of ventricular activity in the ventricular channel, where ventricular activity may be either an R-wave or the generation of a V-pulse, whichever event occurs first. The control system of the pacemaker includes timing means for measuring a natural conduction time interval as the time period between atrial activity in the atrial channel and the sensing of an R-wave in the ventricular channel. In accordance with the present invention, the control system automatically sets the AV time interval to a value that is equal to the natural conduction time interval plus or minus a prescribed amount, which AV time interval value is typically limited to be not less than a minimum AV time interval value, nor greater than a maximum AV time interval value.

For cardiomyopathy patients, the AV interval is set to a value that is less than the natural conduction time interval, and thus (in the absence of a decreasing natural conduction time interval) the pacemaker provides preemptive ventricular pacing, i.e., generates a V-pulse in the ventricular channel prior to the occurrence of an R-wave, thereby advantageously providing a different mechanical contraction sequence that improves the cardiac output of the patient and offers needed therapy for such patients. Further, in the presence of a decreasing natural conduction time interval, the pacemaker may automatically decrease the AV time interval to a value that remains less than the shortest conduction time interval, but which periodically checks the natural conduction time interval so that the AV time interval can be adaptively set to value that remains less than the most recently measured natural conduction time interval by a prescribed amount.

More particularly, the control system of the dual-chamber pacemaker may automatically adjust the AV time interval towards its initial value in the event a prescribed number of consecutive cardiac cycles occur without any change in what is sensed, or not sensed, in the atrial and/or ventricular channels, e.g., without an R-wave having been sensed by the ventricular sense amplifier. In this way, for example, when cardiomyopathy treatment is provided in the form of preemptive ventricular pacing, the AV time interval remains adjusted to a value just less than the most-recently determined conduction time interval for a period of time no longer than the prescribed number of cardiac cycles.

The pacemaker of the present invention thus adaptively adjusts its AV or PV time interval as a function of the most-recently measured natural conduction time interval. The measured natural conduction time may be based on a single PR or AR interval measurement within a single cardiac cycle, or on an average or mean computation (or other appropriate combination) of the PR and/or AR intervals over several cardiac cycles. Typically, the measured natural conduction time will be limited to values between maximum and minimum values. For cardiomyopathy treatment regime, for example, the pacemaker may be configured for preemptive ventricular pacing, i.e., to provide a V-pulse just prior to when an R-wave would otherwise occur. For other types of pacing regimes, the pacemaker may be configured to provide a ventricular stimulation pulse only when a prescribed amount of time has lapsed in excess of the most-recently determined natural conduction time.

It is thus a feature of the present invention to provide an implantable pacemaker and method of operating such a pacemaker that adaptively adjusts its AV or PV interval to a value that is a function of the most recently determined natural conduction time of the patient, e.g., $\pm\Delta$, of $t_{AR}$, where $\Delta$ is a programmed value, e.g., 1–100 msec., and $t_{AR}$ is the most-recently determined natural conduction time.

It is another feature of the invention to provide such a pacemaker that may be selectively configured for treatment of cardiomyopathy through preemptive ventricular pacing, i.e., by stimulating the ventricular cardiac tissue at a time in the cardiac cycle that is just prior to when natural depolarization of the cardiac tissue would otherwise cause a cardiac contraction, thereby altering the mechanical contraction sequence of the heart so as to improve the cardiac output.

It is yet another feature of the invention to provide a dual-chamber pacemaker, and method of operating such a dual-chamber pacemaker, that automatically adjusts its pacemaker-defined AV interval to a value that is just less than (for cardiomyopathy treatment) or just more than (for other pacing regimes) the natural conduction time of a patient. Such pacemaker assures that: (1) for cardiomyopathy treatment a V-pulse is generated and delivered to the ventricular muscle tissue at a time in the cardiac cycle prior to the natural depolarization of the ventricular tissue, or (2) for other pacing treatment, a V-pulse is generated and delivered to the ventricular muscle tissue only after the heart has been afforded an ample opportunity to depolarize on its own based on its own natural conduction time; while still maintaining the approximate cardiac timing set by the most-recently determined natural conduction time.

It is a further feature of the invention to provide a pacemaker, and method of operating such a pacemaker, that when used to treat cardiomyopathy, or otherwise provide preemptive ventricular pacing, decreases the pacemaker-defined AV interval in response to sensing an R-wave (which sensed R-wave evidences a shortened natural conduction time), and that automatically increases the pacemaker-defined AV interval in prescribed increments in response to not sensing an R-wave for a prescribed number of consecutive cardiac cycles (which failure to sense any R-waves may evidence a lengthening of the natural conduction time).

It is yet an additional feature of the invention to provide a pacemaker, and method of operating such pacemaker, that when used, e.g., to provide a demand pacing regime, increases the pacemaker-defined AV interval in response to the absence of a sensed R-wave for a first prescribed number of cardiac cycles (which sustained absence of a sensed R-wave may evidence a lengthened natural conduction time), and that automatically decreases the pacemaker-defined AV interval in a prescribed manner in response to sensing an R-wave for a second prescribed number of cardiac cycles (which sustained sensing of an R-wave evidences a shortening of the natural conduction time).

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker, and a method of operating an implantable dual-chamber pacemaker, that automatically adapts or adjusts its AV interval (or PV interval) to a value that is a function of the most recently determined natural conduction time. The natural conduction time is measured by the pacemaker as the time interval between an atrial event, which could either be a P-wave or an A-pulse, and an R-wave. Throughout the remaining description of the invention, unless the context indicates otherwise, the natural conduction time (whether measured from a P-wave or an A-pulse) is generically referred to as $t_{AR}$. Once the natural conduction time has been determined, the AV (or PV) interval of the pacemaker is set to a value that is a function of $t_{AR}$, e.g., $t_{AR}\pm\Delta$, where $\Delta$ is a programmable number of from, e.g., 1–100 msec. The natural conduction time is thereafter periodically determined, e.g., every x cardiac cycles (where x is a prescribed number, e.g., from 10 to 1024) by the sensing circuits of the pacemaker, so that the AV (or PV) interval can be regularly updated to remain within ±Δ of the most-recently determined $t_{AR}$. In this manner, the AV (or PV) interval used by the pacemaker assumes a value derived from the measured natural conduction time $t_{AR}$ of the patient, and such AV (or PV) interval more or less tracks changes that occur in the natural conduction time.

One application of the invention, and the principal application described hereinafter in more detail, is to treat patients suffering from cardiomyopathy. In such instances, the AV (or PV) interval of the pacemaker is set to a value that is less than the natural conduction time, $t_{AR}$, by a prescribed amount Δ, thereby assuring that ventricular pacing (in the absence of a decreasing $t_{AR}$) will preempt a natural depolarization (R-wave). Such ventricular pacing advantageously alters the mechanical contraction sequence of the cardiac tissue so as to favorably increase the cardiac output of the heart. It is to be understood, however, that even though the principal application of the invention described below relates to treating cardiomyopathy, and therefore involves setting the AV (or PV) interval to a value that is less than the natural conduction time, the invention is not so limited. Rather, the invention relates broadly to determining the natural conduction time $t_{AR}$, and setting the AV (or PV) interval to be a prescribed amount less than or greater than $t_{AR}$.

Figure 7:
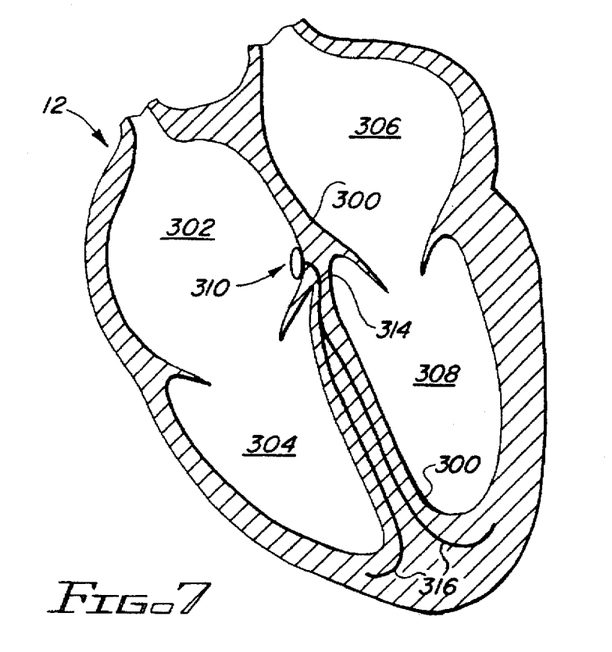
FIG. 7 is a schematic cross-sectional representation of a healthy heart.
Figure 8:
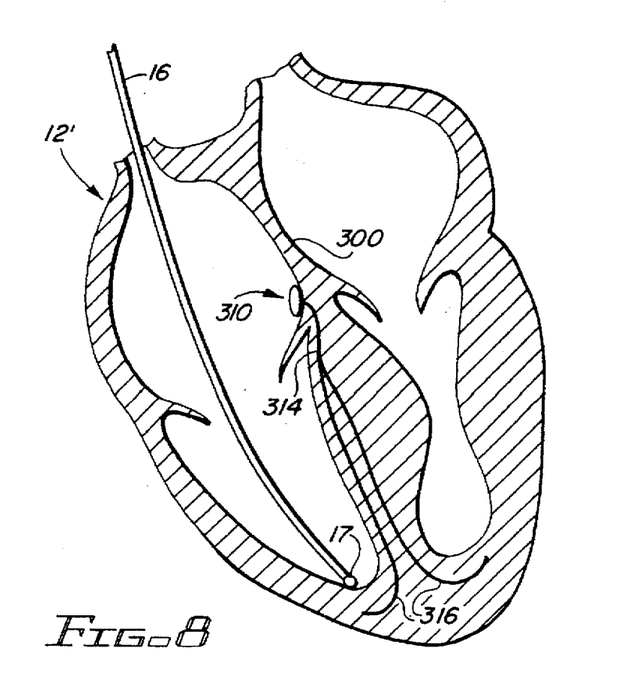
FIG. 8 is a schematic cross-sectional representation of a heart suffering from cardiomyopathy.

In order to explain the effect of cardiomyopathy, reference is first made to FIGS. 7 and 8, where there is shown a schematic cross-sectional representation of a healthy heart 12 (FIG. 7) and a heart 12' suffering from cardiomyopathy (FIG. 8). Referring first to FIG. 7, the heart 12 includes four chambers, a right atrium 302, a right ventricle 304, a left atrium 306, and a left ventricle 308. The right side of the heart is separated from the left side of the heart by a wall of tissue, or septum 300. The AV node 310 is located in the septum 300. The bundle of His 314 and Purkinje fibers 316 also lie in the septum 300. The Purkinje fibers 316 lead from the bundle of His 314 to the apex of the heart. The Purkinje fibers 316 provide a path through which a stimulus is rapidly carried from the AV node 310 to the ventricular tissue, first to the septum, and then throughout the entire ventricular system. In response to a naturally conducted stimulus, the ventricular tissue begins to contract, which forces the blood held in the ventricles out appropriate arteries (not shown) to desired body tissue locations.

In general, the muscle tissue (usually the ventricular muscle tissue) of the heart of a patient suffering from cardiomyopathy is unable to efficiently pump much blood with each normally conducted contraction, either because the heart is not strong enough (e.g., as in dilated cardiomyopathy) or because the heart's outflow tract is obstructed (e.g., as in the case of hypertrophic obstructive cardiomyopathy).

Turning next to FIG. 8, there is shown a schematic representation of a heart 12' that suffers from hypertrophic obstructed cardiomyopathy. Typically, the muscle tissue of the hypertrophic obstructed cardiomyopathic heart is thicker (because it is saggy and full of fatty tissue), and as a result the ventricles may even exhibit less blood-holding capacity than a normal heart. It should be apparent from FIG. 8 that if the septum 300 were to be stimulated from the Purkinje fibers 316, then the left ventricle could pinch off and become obstructed (hence, the name "hypertrophic obstructive cardiomyopathy").

However, when a ventricular stimulation pulse (V-pulse) is provided to the heart at the right time in the cardiac cycle, then a stronger muscle contraction is provided, and the cardiac output (amount of blood pumped by the heart) of the patient increases. The improvement in the cardiac output is caused by the fact that the stimulated contraction of the heart 12' starts at a different location, i.e., at the apex of the heart rather than through the natural conduction system.

Thus, a stimulated contraction advantageously produces a different mechanical or physical sequence of the ventricular contraction (i.e., from the apex and upward) than is achieved through a naturally conducted contraction 316 (FIG. 7). Such different mechanical sequence, in turn, enhances the cardiac output by forcing the blood upward and outward.

Further, for some patients, a continued treatment using preemptive ventricular pacing as described herein results in a marked improvement in cardiac output over time. That is, the continued application of a ventricular stimulus so as to cause a different mechanical contraction sequence appears to cause a thinning of the thick cardiomyopathic walls of the heart, and a strengthening of the ventricular muscle tissue, thereby effecting not only a treatment for cardiomyopathy, but also a cure.

The "right time" to provide a V-pulse in the cardiac cycle to enhance cardiac output is just prior to when the ventricles would naturally beat (depolarize, and hence contract) on their own due to the normal conduction time of the patient, i.e., just prior to the occurrence of an R-wave. To this end, the present invention determines the natural conduction time between a P-wave (evidencing depolarization of the atria) and a subsequent R-wave, or PR interval, and sets the PV interval of the pacemaker to be a prescribed amount less than such PR interval. Alternatively, should the atria of the patient also require stimulation, the invention determines the paced conduction time between an atrial stimulation pulse, (A-pulse) and a subsequent R-wave, or AR interval, and sets the AV interval of the pacemaker to be a prescribed amount less than such AR interval. In this manner, the pacemaker always delivers a V-pulse at the conclusion of the PV or AV intervals, which (for treating cardiomyopathy) is less than the natural conduction time (PR or AR interval), and hence before the ventricles attempt to contract on their own.

Advantageously, the present invention may be implemented using a wide variety of dual-chamber pacemaker configurations and pacemaker hardware. Any pacemaker configuration that allows the pacemaker AV or PV intervals to be automatically set to a value that is a prescribed amount less or more than the AR or PR conduction-time intervals may be used to implement the invention. The description that follows is only exemplary of one such configuration.

Figure 1:
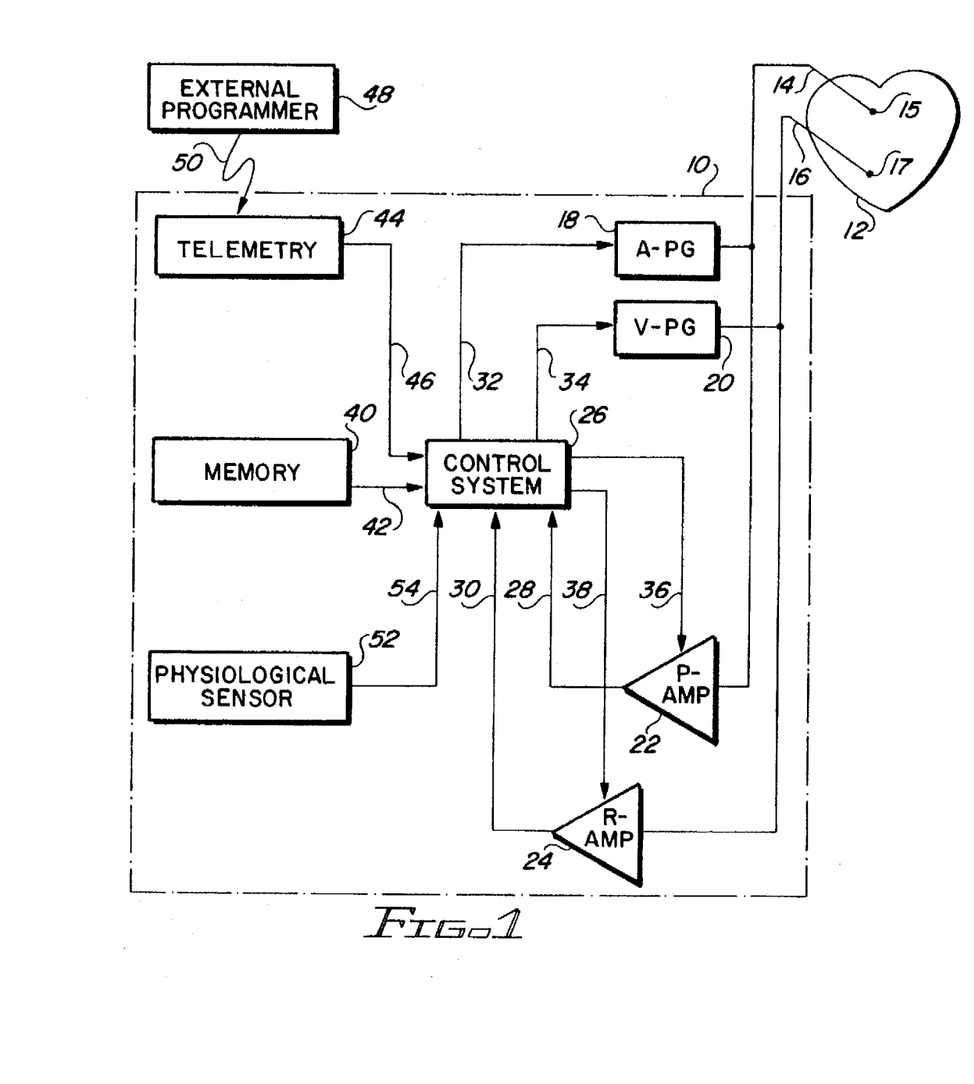
FIG. 1 is block diagram of a dual-chamber programmable pacemaker.

Referring then to FIG. 1, a block diagram of a dual-chamber pacemaker 10 is illustrated. The pacemaker 10 is coupled to a heart 12 by way of leads 14 and 16. The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

A control system 26 controls the dual-chamber pacer 10. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also prevents the sensing of residual electrical signals that may be present in the muscle tissue as a result of the pacer stimulation, which sensing could falsely be interpreted as P-waves or R-waves.

Still referring to FIG. 1, the pacer 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed atrial escape interval (AEI). Further, data sensed during the operation of the pacer may be stored in the memory circuit 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory circuit 40) may be remotely received from the pacer 10. In this manner, noninvasive communications can be established from time to time with the implanted pacer 10 from a remote, non-implanted, location. See, e.g., U.S. Pat. No. 4,847,617, issued to Silvian, entitled "High Speed Digital Telemetry System for Implantable Devices," incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel.

In accordance with one embodiment of the present invention, the pacemaker 10 may further include one or more sensors 52 that is/are connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of sensors, such as physiologic sensors that sense the oxygen content of blood, respiration rate, pH of blood, and the like, may also be used in lieu of, or in addition to, an activity sensor. The type of sensor, if any, used is not critical to the present invention. Any sensor or combination of sensors capable of sensing body motion or a physiological parameter relatable to the rate at which the heart should be beating can be used. A pacemaker using such sensors is commonly referred to as a "rate-responsive" pacemaker because such a pacemaker adjusts the rate (escape interval) of the pacer in a manner that tracks the physiological needs of the patient.

Figure 2:
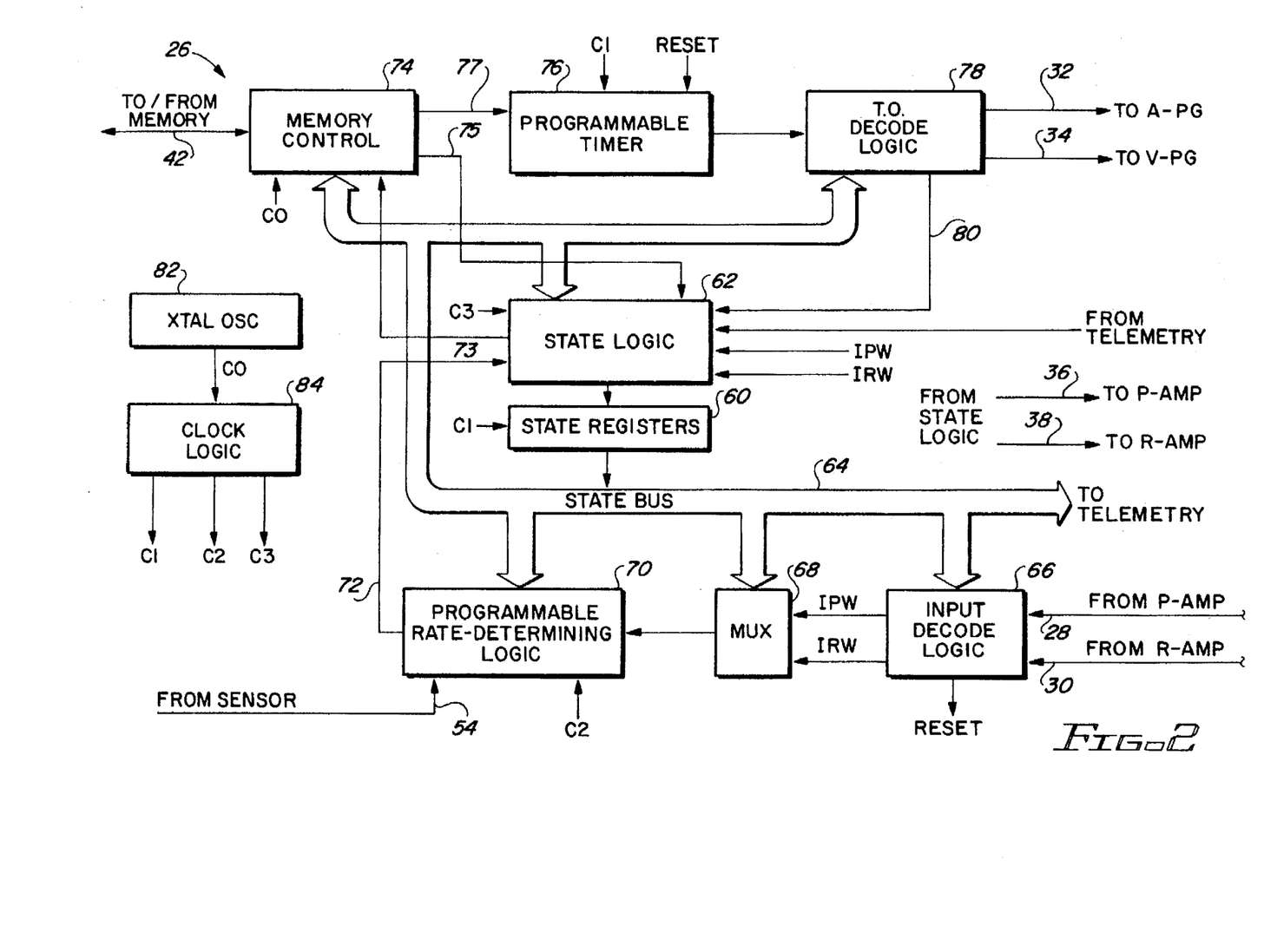
FIG. 2 is a block diagram of one embodiment of the control logic of the pacemaker of FIG. 1.

Referring next to FIG. 2, a block diagram of one embodiment of the control system 26 of the pacer 10 is illustrated. It is noted that other embodiments of a control system 26 may also be utilized, such as a microprocessor-based control system. A representative microprocessor-based system is described, for example, in commonly-assigned U.S. Pat. 4,940,052, entitled "Microprocessor Controlled Rate-Responsive Pacemaker Having Automatic Threshold Adjustment," which patent is incorporated herein by reference.

The control system shown in FIG. 2 is based on a state machine wherein a set of state registers 60 define the particular state of the pacer at any instant in time. In general, and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine, such as is described in the above-cited patent. The telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (Inhibiting P-Wave) and "IRW" (Inhibiting R-Wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal from the sensor 52 (FIG. 1) over signal line 54, and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 2, a memory control circuit 74 provides the needed interface between the circuits of the control system 26 and the memory circuit 40 (FIG. 1). This memory control circuit 74 may be any conventional memory access circuit that sends or receives data over data/address bus 42 to or from the memory circuit 40 at a specified address. Data retrieved from the memory circuit 40 may be sent to either the state logic 62 (over signal line(s) 75) or to one or more programmable timers 76 (over signal line(s) 77). Data sent to the memory circuit 40 may be either the current state of the system (obtained off of the state bus 64), or other selected signals from the state logic (as made available over signal line(s) 73).

The programmable timer 76 defines a prescribed time interval, the length of which is set by the signal(s) received from the memory control 74 over signal line(s) 77, and the starting point of which begins coincident with the start of the current state, as obtained from the state bus 64 through the memory control circuit 74. The timer 76 further generates a time-out (T.O.) signal when this prescribed time interval has elapsed. During the prescribed time interval, the timing function may be reset by a reset signal, typically obtained from the input decode logic 66, although some states (as obtained from the state bus 64) may also effectuate an immediate reset of the timer 76. The time-out signal is sent to time-out decode logic 78. It is the function of the time-out decode logic to generate the appropriate trigger signals that are sent to the A-pulse generator 18 or the V-pulse generator 20 (FIG. 1) by way of signal lines 32 and 34, respectively. Further, an appropriate logic signal(s) is sent to the state logic 62 by the time-out decode logic 78 over signal line(s) 80 in order to notify the state logic that the respective trigger signals have been generated. It is to be understood that while FIG. 2 only shows one programmable timer 76, several such programmable timers may be used, as is required, in order to simultaneously keep track of multiple time intervals.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2, and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25–40 KHz for the basic clock rate C0 is adequate. This rate provides a basic time increment of 25–40 microseconds each clock cycle, and this is more than enough time to effectively control the pacemaker operation. If desired, a faster basic clock rate can be used, particularly by the memory control circuit 74, to speed up the data transfer between the control system 26 and the memory circuit 40, although for most pacemaker operations, a fast data transfer rate is not essential.

In operation, the control system of FIG. 2 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as a V-A Interval (VAI) state wherein a prescribed ventricular-to-atrial (V-A) interval is initiated. For purposes of the present invention, this V-A interval may be considered as the "atrial escape interval," or "AEI." As soon as the memory control circuit 74 detects that the VAI state has been initiated, as evidenced by the "1000" appearing on the state bus 64, it retrieves from the memory circuit 40 an appropriate data word, previously programmed into the memory circuit 40 from the external programmer 48 (FIG. 1), or otherwise generated by the state logic 62, that defines the desired length of the AEI. This data word is sent to the programmable timer and sets the length of the time period that is to be measured during the VAI state.

The timer 76 is essentially just a counter that counts down (or counts up), using a specified clock signal, to the value specified in the data word. When the counting has been completed, and assuming that the counter has not been reset by the occurrence of a P-wave or other sensed event, the counter or timer 76 is said to have "timed-out," and an appropriate timed-out signal is generated and sent to the timed-out decode logic 78. The decode logic, in turn, recognizes that the current state of the system is the VAI state (as determined by monitoring the state bus 64), and therefore that the AEI has timed-out without any cardiac activity having been sensed. Hence, an A-pulse trigger signal is generated and sent to the A-pulse generator 18, so that the atrium can be stimulated. At the same time, an appropriate logic signal(s) is sent to the state logic 62 over the signal line(s) 80 to alert the state logic to the fact that the timer 76 has timed-out.

The state logic 62, in response to receiving the signal(s) from the time-out decode logic 78, and also in response to the current VAI state, triggers the next state of the prescribed sequence. For DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 60 assuming a "0001" (hex "1") condition. This BLANK state, detected on the state bus 64, causes the memory control circuitry 74 to retrieve an appropriate data word from the memory circuit 40 that defines the length of the blanking interval, which data word is loaded into the programmable timer 76. As soon as the timer 76 times-out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 60 to assume the next state in the prescribed sequence, which may be, for example, an AV-Interval state.

At the beginning of the AV-Interval state, another value is loaded into the programmable timer 76, or into an equivalent programmable timer, that defines the length of the pacemaker-defined AV interval, or "AVI." If the timer 76 times-out without being reset, indicating that no R-wave has been sensed, the decode logic generates a V-pulse trigger signal, and notifies the state logic 62 of this event. The state logic, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

In the manner described above, the control system 26 assumes one state after another, thereby controlling the operation of the pacemaker. In general, a state is changed when the timer 76, or an equivalent timer, times-out, or when a prescribed event occurs. Further, in accordance with the present invention, if a prescribed event occurs (e.g., the occurrence of a P-wave), then the next state may be a PV-Interval state. The PV-Interval state is the same as the AV-Interval state, described above, except that a different value is loaded into the programmable timer 76, which different value defines the length of the PV interval, or "PVI".

It is noted that the state of the control system could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD or VDI, for example, can be defined by appropriate control of the memory control circuit 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 will not be presented herein because all such circuits may be conventional, or may be patterned after known circuits available in the art. Reference is made, for example, U.S. Pat. No. 4,712,555, wherein a state-machine type of operation for a pacemaker is described; U.S. Pat. No. 4,788,980, wherein the various timing intervals used within the pacemaker and their interrelationship are more thoroughly described; and U.S. Pat. No. 4,944,298, wherein an atrial-rate based programmable pacemaker is described, including a thorough description of the operation of the state logic used to control such a pacemaker. The '555, '980 and '298 patents are incorporated herein by reference.

Figure 3:
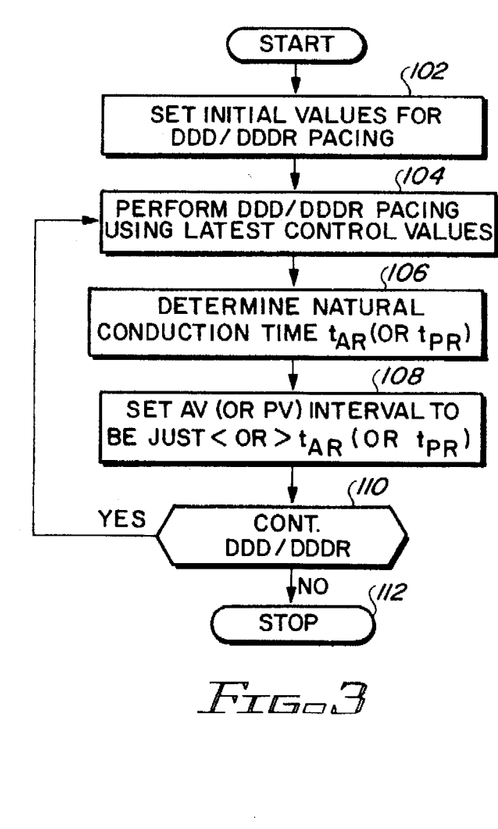
FIG. 3 is a flowchart illustrating the method of the present invention.

Of primary significance to the present invention is the manner in which the AV interval (or PV interval) is adaptively adjusted as a function of the measured natural conduction time of the patient. The manner in which this is done is illustrated in the flowchart of FIG. 3. In FIG. 3, as well as the other flowcharts presented herein, each main step of the method being described is illustrated as a "box" or "block". Reference numerals are assigned to each block of the flowchart to aid in the description of the invention that follows. Each step of the method, i.e., each block, may be readily carried out by those of skill in the art by programming appropriate "code" in the memory circuit 40, which code causes the necessary control signals to be generated to carry out the desired steps. Equivalent techniques for generating the control signals needed to carry out the prescribed method or sequence may also, of course, be used.

As seen in FIG. 3, the method starts by setting the initial values needed by the pacemaker to carry out DDD or DDDR pacing (block 102). Such values are, for the most part, no different than those used when performing conventional DDD or DDDR pacing, and include such values as an initial pacing rate (from which an appropriate atrial escape interval is determined), an initial value for the AV interval, blanking period values, maximum pacing rate values, stimulation pulse amplitudes and widths, and the like. In accordance with the present invention, such initial values also include a minimum and maximum value for the AV (or PV) interval, plus a prescribed time difference between the natural conduction time of the patient and the pacemaker-defined AV (or PV) interval. In some embodiments of the invention, it may also be important to specify the difference between the AV interval and a PV interval, where the AV interval is the natural conduction time as measured from the delivery of an A-pulse to the subsequent occurrence of an R-wave, and the PV interval is the natural conduction time as measured from the occurrence of a P-wave to the subsequent occurrence of an R-wave.

Once the initial values needed to carry out DDD or DDDR pacing have been set, the specified DDD or DDDR pacing is carried out (block 104) in conventional manner, one cardiac cycle at a time, using the programmed values. At some point in a cardiac cycle associated with such DDD or DDDR pacing, an R-wave will occur; or a number of consecutive cardiac cycles will go by without the occurrence of an R-wave. Either event, or the occurrence of other prescribed events, such as the passage of a prescribed number of cardiac cycles (e.g., x cardiac cycles, where x is a number from 10 to 2048) or the mere passage of time (e.g., once every 10–15 minutes), may be used to signal a need to determine the natural conduction time of the patient (block 106). Once such need is identified, an appropriate adjustment to the AV (or PV) interval of the pacemaker can be made, as required (block 108).

The occurrence of an R-wave indicates the depolarization of the ventricles as a result of a natural or native conduction time shorter than the presently existing AV (or PV) interval of the pacemaker. Hence, when preemptive ventricular pacing is desired (such as when treating cardiomyopathy), such event indicates that the pacemaker-defined AV (or PV) interval needs to be decreased. Alternatively, when demand pacing is desired, such event (if it occurs over a sufficiently long period or time or number of cycles) may indicate that the natural conduction time has increased, and that the pacemaker-defined AV (or PV) interval may also be increased. Accordingly, as soon as an appropriate criteria is met (such as the repeated occurrence of an R-wave, the passage of time, or the completion of a prescribed number of cardiac cycles), which criteria indicates that the natural conduction time, $t_{AR}$, should be determined or remeasured, then $t_{AR}$ is measured or otherwise determined (block 106).

The natural conduction time is determined as the time interval between the most recent atrial activity, which would be either a P-wave or an A-pulse, and an R-wave. That is, the native or natural conduction time begins with the occurrence of atrial activity, and ends with the occurrence of an R-wave. If the most recent atrial activity was a P-wave, then the conduction time measured is $t_{PR}$. If the most recent atrial activity was an A-pulse, then the conduction time measured is $t_{AR}$. (Note, heretofore $t_{AR}$ has been used to refer generically to the natural conduction time, whether technically $t_{PR}$ or $t_{AR}$). In order to assure that the determination of $t_{AR}$ or $t_{PR}$ accurately reflects the true natural conduction time, the natural conduction time over several cardiac cycles may be measured, and then an average, mean, or other appropriate combination, of $t_{AR}$ or $t_{PR}$ over the prescribed number of cycles can be computed.

If an R-wave fails to occur for a prescribed number of cardiac cycles, then that provides an indication that perhaps the natural conduction time has increased, and that there is a need to increase the AV (or PV) interval so that it is not too different than the natural conduction time.

Once a determination is made that the natural conduction time has either decreased or increased (block 106), the AV (or PV) interval of the pacemaker is then set to a value that is just less than or just more than, depending upon the application, the determined natural conduction time. This is done by setting the AV (or PV) interval to be equal to the most recent $t_{AR}$ (or $t_{PR}$) determination $\pm \Delta$, where $\Delta$ is a programmable value, typically ranging from 5–40 msec. Whether $\Delta$ is added to or subtracted from the natural conduction time will be determined by the particular application at hand. For example, when the pacemaker is used to treat cardiomyopathy, and when it appears that the natural conduction time has decreased (as is most often the case when an R-wave has been sensed), then the AV (or PV) interval is set to $t_{AR}$ (or $t_{PR}$) minus $\Delta$; and when it appears that the natural conduction time may have increased (as is most often the case when an R-wave has not been sensed for a prescribed number of cardiac cycles), then the AV (or PV) interval may set to $t_{AR}$ (or $t_{PR}$) plus $\Delta$.

After the AV (or PV) intervals have been set to be less than or more than the determined conduction time $t_{AR}$ (or $t_{PR}$) at block 108, then a determination is made as to whether DDD or DDDR pacing is to continue (block 110). If not, then the method terminates (block 112). If so, then the method continues (block 104) by performing the DDD or DDDR pacing for the next cardiac cycle using the adjusted values of the AV (or PV) interval.

Figure 4:
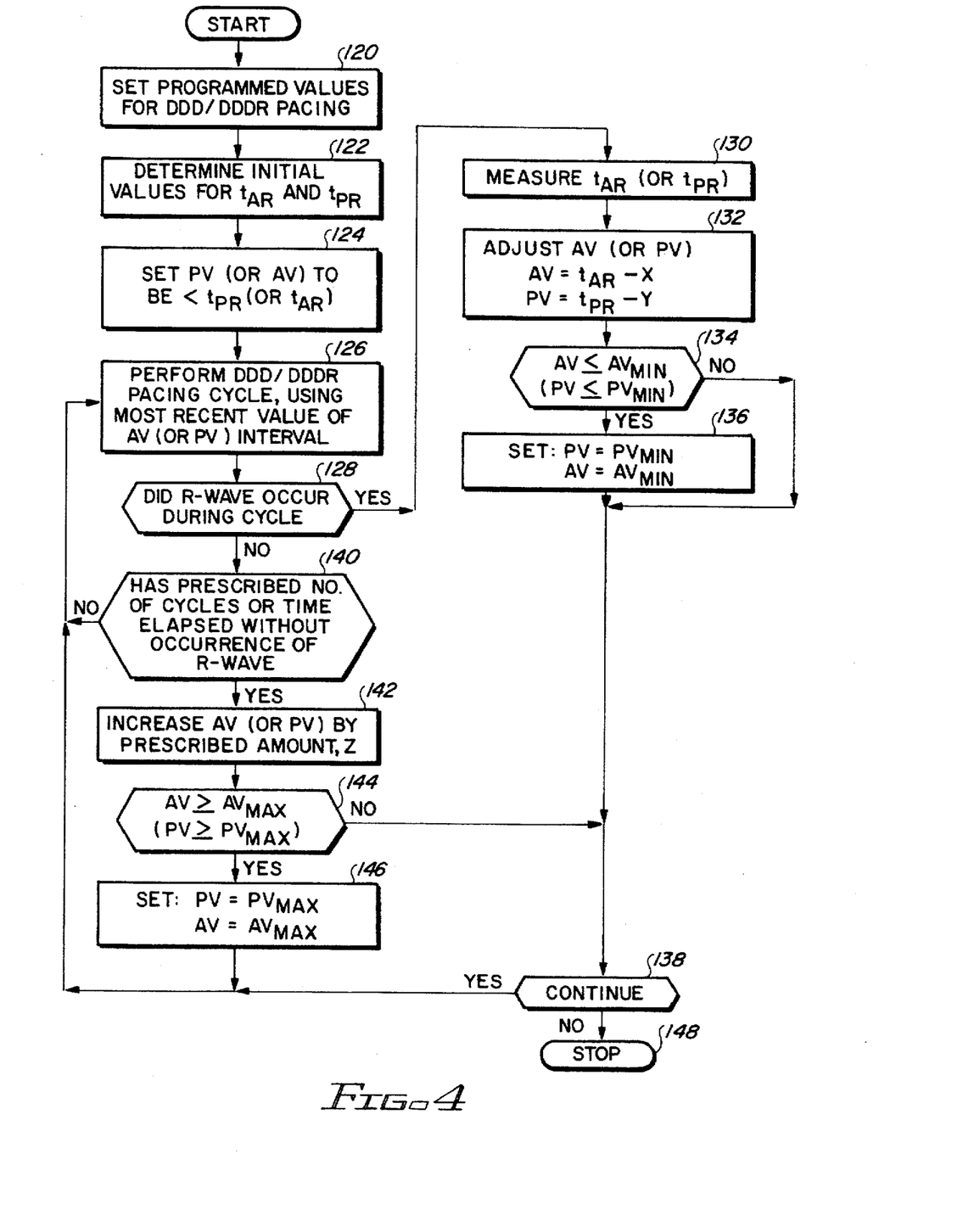
FIG. 4 is a more detailed flowchart illustrating the method of the present invention when used to provide preemptive ventricular pacing to treat cardiomyopathy.
Figure 5:
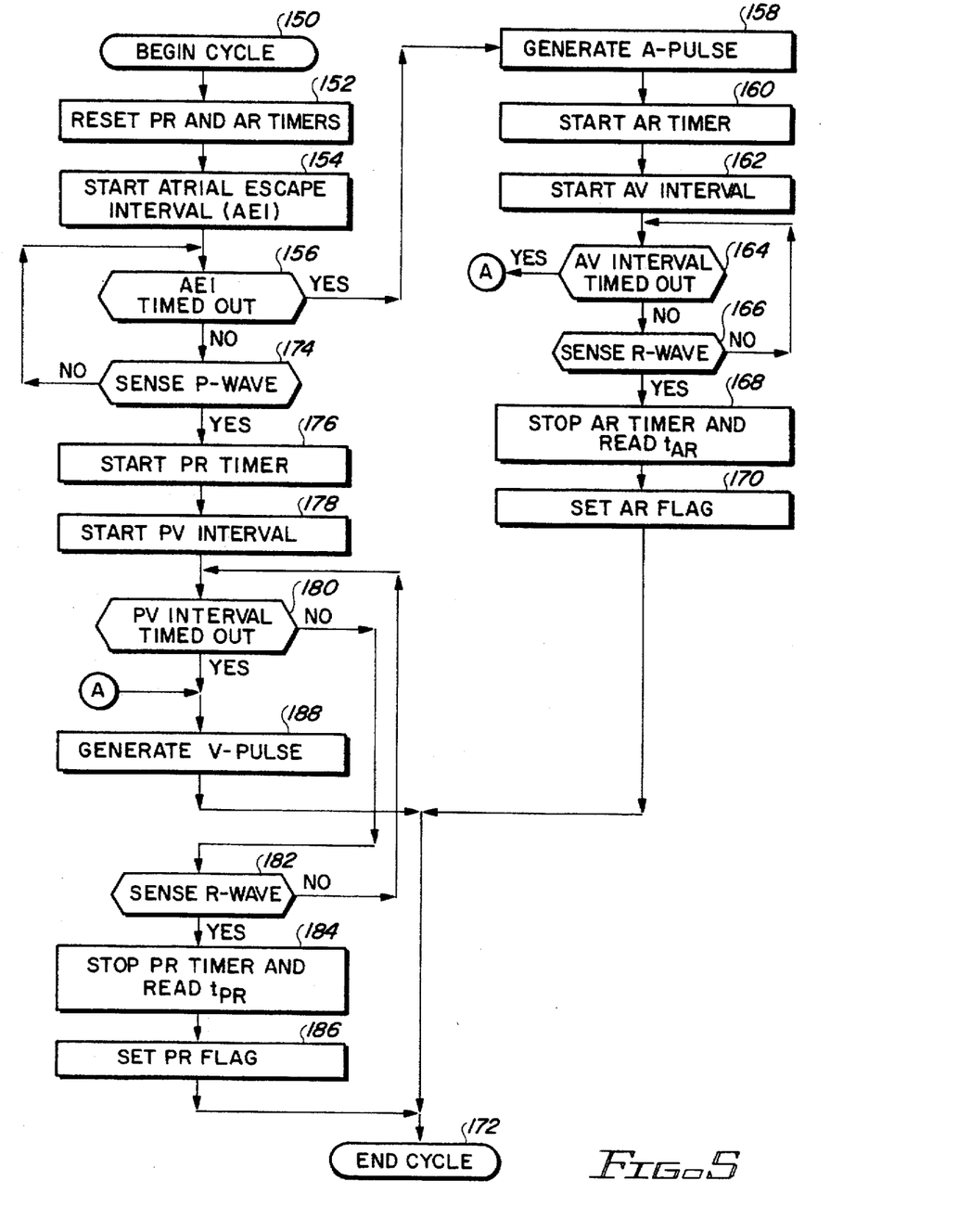
FIG. 5 is a flowchart that illustrates one technique for measuring the natural conduction time of a patient.
Figure 6:
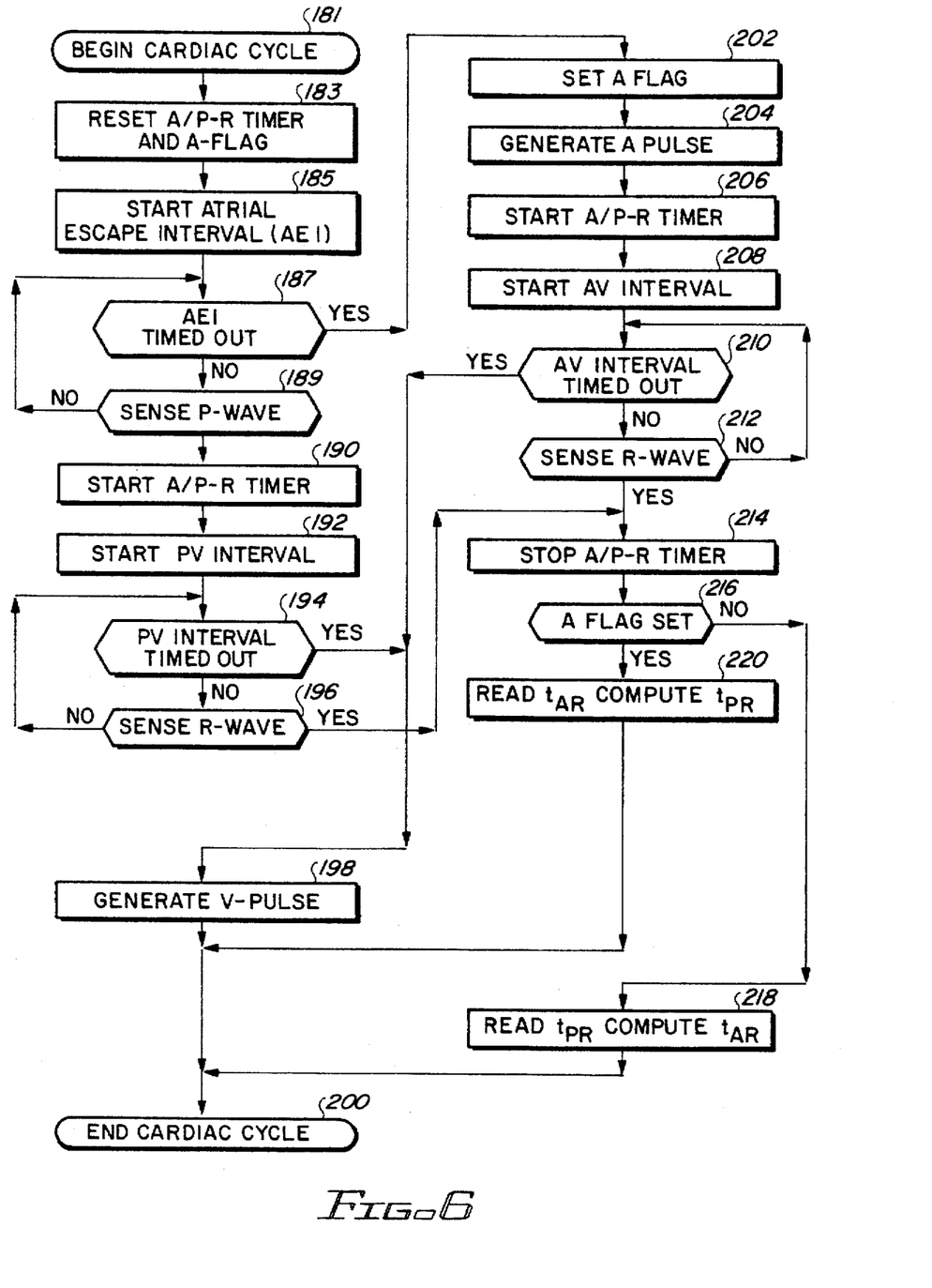
FIG. 6 is a flowchart that illustrates another embodiment for determining the natural conduction time of a patient, wherein one of the PR or AR conduction time intervals is measured, and the other is set as a prescribed difference from the measured value.

Turning next to FIG. 4, a more detailed flowchart is illustrated that shows one technique for determining or measuring the natural conduction time of the patient (block 106 in FIG. 3), and adjusting the AV (or PV) intervals accordingly (block 108 in FIG. 3). It is noted that the method shown in FIG. 4, as well as the methods shown in FIGS. 5 and 6, are directed primarily to using the pacemaker to treat cardiomyopathy, i.e., are directed to a method that provides preemptive ventricular pacing. However, such methods may be readily adapted by those of skill in the art for other applications of the invention.

In FIG. 4, the programmed values needed to carry out DDD or DDDR pacing are programmed into the pacemaker in conventional manner (block 120). In accordance with the present invention, such programmed values include the number of cardiac cycles that must occur without an R-wave before the AV (or PV) interval is increased, the amount of such increase, an initial value for the natural conduction time $t_{AR}$ (or $t_{PR}$), or an indication of a technique for determining such initial values, the difference X and/or Y between the natural conduction times and the AV (or PV) intervals, and the like (block 122). Once the initial values of $t_{AR}$ or ($t_{PR}$) have been determined, then the value of the AV (or PV) interval is set to be a specified amount (e.g., $\Delta$) less than $t_{AR}$ or $t_{PR}$ (block 124). While FIG. 4 describes one embodiment for a patient suffering from cardiomyopathy (i.e., using an AV/PV interval less than the measured conduction time), it is within the spirit of the invention to modify block 124 to set the AV/PV interval greater than the measured conduction time for patients that would benefit from their own conduction.

With the AV (or PV) interval set to an initial value, the DDD or DDDR pacing cycle commences using such value, plus the other programmed values (block 126). If an R-wave is sensed during the pacing cycle (block 128), then that signals that the natural conduction time $t_{AR}$ (or $t_{PR}$) is shorter than the pacemaker-defined AV (or PV) interval. The occurrence of the R-wave indicates the end of the conduction time $t_{AR}$ (or $t_{PR}$), and thus permits a measurement of $t_{AR}$ (or $t_{PR}$) to be completed (block 130). Two different measurement techniques for determining $t_{AR}$ (or $t_{PR}$) are detailed more fully in FIGS. 5 and 6. The measured value of $t_{AR}$ (or $t_{PR}$) is then used as a basis for decreasing the AV (or PV) interval (block 132). The AV interval is set to $t_{AR}$–X, where X is a parameter having a programmable value, a fixed value, or an adaptive value based on a percentage of the heart rate. Similarly, the PV interval is set to $t_{PR}$–Y, where Y is a parameter having a programmable value, a fixed value, or an adaptive value based on a percentage of the heart rate.

As is described more fully below in conjunction with FIGS. 5 and 6, in some embodiments of the invention, $t_{PR}$ and $t_{AR}$ are measured separately, and separate values are programmed or otherwise determined for the parameters X and Y. Thus, in such embodiments, $t_{PR}$ and the resulting PV interval, and $t_{AR}$ and the resulting AV interval, are totally independent of each other. In other embodiments, one of $t_{AR}$ or $t_{PR}$ is determined, whichever happens to occur first, and the other is computed as a function of the measured value. In such embodiments, there is thus a prescribed relationship between $t_{AR}$ and $t_{PR}$ and the resulting AV and PV intervals. For most purposes relating to the description of the present invention, one of the AV (or PV) intervals, or one of the conduction times $t_{AR}$ (or $t_{PR}$), is all that is expressly referenced, and it is assumed that the other can be determined in an appropriate manner.

After the AV (or PV) interval has been set to its new value based on the most recent measured value of $t_{AR}$ (or $t_{PR}$) (block 132), a determination is made as to whether the new value of the AV (or PV) interval is less than or equal to a programmed minimum value for the AV (or PV) interval, $AV_{MIN}$ (or $PV_{MIN}$) (block 134). If so, then the AV (or PV) interval is set to $AV_{MIN}$ (or $PV_{MIN}$). If not, then the AV (or PV) interval maintains the value previously determined. If DDD (or DDDR) pacing is to continue (block 138), then the next cycle of such pacing continues using the newly set value of the AV (or PV) interval (block 126).

Should an R-wave not occur during the pacing cycle (block 128), then a determination is next made (block 140) as to whether a prescribed (programmed) number of cardiac cycles have occurred without the occurrence of an R-wave. If not, then the next cycle begins (block 126). If yes, then that indicates that perhaps the natural conduction time has increased, and that the AV (or PV) interval should also be increased to keep the difference between such natural conduction time and the AV (or PV) intervals to a minimum. Accordingly, the AV (or PV) interval is increased by a prescribed amount, Z (block 142). The value Z may be a fixed value, a programmable value, or an adaptive value based on a percentage of heart rate. After the AV (or PV) interval has been increased, a determination is made as to whether the new value of the AV (or PV) interval is greater than or equal to a programmed maximum value for the AV (or PV) interval, $AV_{MAX}$ (or $PV_{MAX}$) (block 144). If so, then the AV (or PV) interval is set to $AV_{MAX}$ (or $PV_{MAX}$). If not, then the AV (or PV) interval maintains the value previously determined (at block 142). If DDD (or DDDR) pacing to continue (block 138), then the next cycle of such pacing continues using the newly set value of the AV (or PV) interval (block 126). If not, then the method terminates (block 148).

The number of cardiac cycles that must occur without the occurrence of an R-wave before the AV (or PV) interval is increased is preferably a programmable number, and may typically be anywhere from 8 to 128 cycles or more. Alternatively, a specific time interval may be specified, 2–10 minutes, that must elapse without the occurrence of an R-wave before the AV (or PV) interval is increased. The amount Z by which the AV (or PV) interval is incrementally increased is also preferably a programmable value, but could be a fixed value, or an adaptive value. Typical values for Z range from 5–40 msec.

Referring next to FIG. 5, a flowchart is shown that illustrates one technique for measuring the natural conduction times, $t_{AR}$ and $t_{PR}$, during one or more cardiac cycles of the heart. The technique shown in FIG. 5 makes an independent measurement of both $t_{AR}$ and $t_{PR}$. As seen in FIG. 5, at the beginning of the cardiac cycle (block 150), a PR timer and an AR timer are reset (block 152). Such timers, as well as the other timers referenced herein, may be implemented in hardware or software within the control system 26 (FIGS. 1 and 2).

After resetting such timers, an atrial escape interval (AEI) begins (block 154). If a P-wave is not sensed during the AEI (blocks 156, 174), then an A-pulse is generated (block 158), and the AR timer commences (block 160). Also, the AV interval begins (block 162). If an R-wave occurs during the AV interval (blocks 164, 166), then the AR timer is stopped, and the value of the AR timer represents a measure of the conduction time $t_{AR}$ (block 168). An AR flag is then set (block 170), and the cardiac cycle ends (block 172), having determined $t_{AR}$ during the cycle.

If the AV interval times-out without detecting an R-wave (block 164), then a V-pulse is generated (block 188), and the cardiac cycle ends (block 172), having made no determination of either $t_{AR}$ or $t_{PR}$ during the cycle. Thus, the value of $t_{AR}$ and/or $t_{PR}$ used at the beginning of the cardiac cycle is retained as the conduction time value used for the next cardiac cycle.

Should a P-wave be sensed before the AEI times-out (blocks 156, 174), then the PR timer is started (block 176). Also, the PV interval is started (block 178). If an R-wave occurs during the PV interval (blocks 180, 182), then the PR timer is stopped, and the value of the PR timer represents a measure of the conduction time $t_{PR}$ (block 184). A PR flag is then set (block 186), and the cardiac cycle ends (block 172), having determined $t_{PR}$ during the cycle.

It is noted that the AR and PR flags that are set during the cardiac cycle, depending upon whether a P-wave or an A-pulse occurs, may be used during the operation of the pacemaker to steer the adjustment of the AV interval (if the AR flag is set), or the PV interval (if the PR flag is set).

Turning next to FIG. 6, a flowchart of another embodiment or technique for determining the natural conduction time of a patient is illustrated. The technique shown in FIG. 6 determines just one of $t_{AR}$ or $t_{PR}$, and the other is set as a prescribed difference from the measured value. Thus, as seen in FIG. 6, once the cardiac cycle begins (block 181), a single timer, designated as the A/P-R Timer, is reset, as is a single flag, designated the A-Flag (block 183). The atrial escape interval (AEI) is started (block 185), and a determination is made as to whether a P-wave is sensed before the timing out the AEI (blocks 187, 189). If so, then the A/P-R Timer is started (block 190), and the PV interval is started (block 192). While the PV interval is timing out, a determination is made as to whether an R-wave occurs (blocks 194, 196). If an R-wave does occur during the PV interval, then the A/P-R Timer is stopped (block 214), and a determination is made as to whether the A-Flag is set (block 216). If the A-Flag is not set, then that signals that the A/P-R Timer contains the $t_{PR}$ value, which $t_{PR}$ value may be read from the A/P-R Timer, and the $t_{AR}$ value may be computed therefrom (block 218). The cardiac cycle is then completed (block 200) having measured a value of $t_{PR}$ and computed a value of $t_{AR}$ during the cycle.

If the PV interval times-out without sensing an R-wave (blocks 194, 196), then a V-pulse is generated (block 198), and the cardiac cycle terminates (block 200) without having determined a new value for the conduction time $t_{AR}$ or $t_{PR}$. Hence, the next cardiac cycle starts using the previously determined values of $t_{AR}$ or $t_{PR}$.

If the AEI times-out without having sensed a P-wave (blocks 187, 189), then the A-Flag is set (block 202), and an A-pulse is generated (block 204). Also, the A/P-R Timer is started (block 206), and the AV interval is started (block 208). While the AV interval is timing out, a determination is made as to whether an R-wave occurs (blocks 210, 212). If an R-wave does occur during the AV interval, then the A/P-R Timer is stopped (block 214), and a determination is made as to whether the A-Flag is set (block 216). If the A-Flag is set, then that signals that the A/P-R Timer contains the $t_{AR}$ value, which $t_{AR}$ value may be read from the A/P-R Timer, and the $t_{PR}$ value may be computed therefrom (block 220). The cardiac cycle is then completed (block 200) having measured a value of $t_{AR}$ and computed a value of $t_{PR}$ during the cycle.

If the AV interval times-out without sensing an R-wave (blocks 210, 212), then a V-pulse is generated (block 198), and the cardiac cycle terminates (block 200) without having determined a new value of the conduction times $t_{AR}$ or $t_{PR}$. Hence, the next cardiac cycle starts using the previously determined values of $t_{AR}$ or $t_{PR}$.

Thus, it is seen that the present invention provides an implantable pacemaker, and method of operating such a pacemaker, that sets the AV (or PV) interval of the pacemaker to a value that is derived from the measured natural conduction time of the patient. For treating cardiomyopathy, for example, such pacemaker and method stimulates the cardiac tissue at a time in the cardiac cycle that is just prior to when natural depolarization of the cardiac tissue would otherwise cause a cardiac contraction, and in so doing, creates a mechanical contraction sequence that, for most patients, improves the cardiac output.

As further described above, it is seen that the invention provides a dual-chamber pacemaker, and method of operating such a dual-chamber pacemaker, that automatically sets and adjusts the pacemaker-defined AV (or PV) interval to a value that is keyed from the natural conduction time of the patient. Such action advantageously causes a V-pulse to be generated and delivered to the ventricular muscle tissue at a time in the cardiac cycle that suits a particular purpose (e.g., treating cardiomyopathy or providing demand pacing), while still maintaining the approximate cardiac timing set by the natural conduction time.

As also described above, and for use with cardiomyopathy treatment, it is seen that the invention provides a dual-chamber pacemaker, and method of operating such a pacemaker, that decreases the pacemaker-defined AV interval in response to sensing an R-wave (which sensed R-wave evidences a shortened natural conduction time), and that automatically increases the pacemaker-defined AV interval in prescribed increments in response to not sensing an R-wave for a prescribed number of consecutive cardiac cycles (which failure to sense any R-waves may evidence a lengthening of the natural conduction time). Thus, advantageously, the pacemaker-defined AV interval is most always set to a value that is just somewhat less than the natural conduction time, regardless of whether the natural conduction time is increasing or decreasing, and the cardiac output of the patient is maximized.

While the invention herein disclosed has been described by means of specific embodiments and applications thereof, numerous modifications and variations could be made thereto by those skilled in the art without departing from the scope of the invention set forth in the claims.

What is claimed is:

1. A method of treating cardiomyopathy using an implanted dual-chamber pacemaker to provide preemptive ventricular pacing, the pacemaker having an atrial channel and a ventricular channel, means for sensing atrial activity in the atrial channel and natural ventricular activity (an R-wave) in the ventricular channel, a pulse generator that generates a ventricular stimulation pulse (V-pulse) in the ventricular channel at the conclusion of an AV/PV interval that commences with atrial activity and is reset with a sensed R-wave, said method comprising:

(a) measuring a natural conduction time interval as the elapsed time between atrial activity and an R-wave in a given cardiac cycle;

(b) automatically setting the AV/PV interval of the pacemaker to a prescribed amount less than the natural conduction time determined in step (a); and (c) generating the V-pulse at the conclusion of the AV/PV interval to preemptively stimulate the ventricular channel before natural ventricular activity can occur.

2. The method of claim 1, wherein step (a) comprises periodically measuring the natural conduction time interval every x cardiac cycles, where x is an integer between 10 and 2048.

3. The method of claim 1, wherein step (a) comprises measuring the natural conduction time interval for y consecutive cardiac cycles and computing an average of the natural conduction time interval measurements thus made, where y is an integer.

4. The method of claim 1, wherein step (b) comprises setting the AV/PV interval of the pacemaker to a value that is from 1–100 msec less than the natural conduction time.

5. The method of claim 1, wherein step (c) comprises applying the V-pulse through the ventricular channel to a ventricular location adapted to create a mechanical contraction sequence different from the contraction sequence resulting from natural ventricular activity.

6. A method of operating a dual-chamber implantable pacemaker in order to maximize cardiac output of a patient by pacing in the ventricle, if needed, at a time in a cardiac cycle that is near the patient's natural conduction time, the pacemaker having a PV/AV interval that defines the maximum time permitted by the pacemaker after atrial activity before a ventricular stimulation pulse (V-pulse) is generated, comprising:

(a) measuring a PR/AR interval as the time interval between atrial activity and a natural ventricular depolarization (R-wave), where atrial activity comprises either a natural atrial depolarization (P-wave) or an atrial stimulation pulse (A-pulse), whichever occurs first in a given cardiac cycle;

(b) setting the PV/AV interval of the pacemaker to be equal to the measured PR/AR interval ±Δ, where Δ is a prescribed time increment; and (c) repeating steps (a) and (b) in accordance with a prescribed schedule so that the PV/AV interval of the pacemaker tracks the measured PR/AR interval within ±Δ, and so that a V-pulse is generated and applied to the patient's ventricle at the conclusion of the PV/AV interval in each cardiac cycle in which an R-wave does not occur.

7. The method of claim 6, wherein the prescribed schedule of step (c) comprises periodically measuring the natural conduction time interval every x cardiac cycles, where x is an integer between 10 and 2048.

8. The method of claim 6 wherein the prescribed schedule of step (c) comprises periodically measuring the natural conduction time interval every k seconds, where k is an integer.

9. The method of claim 8, wherein k is at least 30 seconds.

10. The method of claim 6, wherein the prescribed schedule of step (c) comprises measuring the natural conduction time interval whenever either: (1) n consecutive cardiac cycles occur without an R-wave being sensed, where n is a first prescribed integer; or (2) m consecutive cardiac cycles occur with an R-wave being sensed in each cycle, where m is a second prescribed integer, whichever occurs first.

11. The method of claim 10, wherein n and m are at least five.

12. A method of treating cardiomyopathy using an implanted dual-chamber pacemaker, the pacemaker having means for sensing atrial and ventricular events, and means for generating a ventricular stimulation pulse (V-pulse) and delivering the V-pulse to a prescribed ventricular location, said method comprising:

(a) determining a natural conduction time as the difference between an atrial event and a natural ventricular event within a given cardiac cycle; and (b) generating and delivering the V-pulse to the prescribed ventricular location at a time, following an atrial event in each cardiac cycle, that is less than the natural conduction time determined in step (a), whereby the V-pulse preempts a natural ventricular event in the presence of a substantially constant natural conduction time, the V-pulse thus delivered triggering a mechanical contraction sequence that improves cardiac output.

13. The method of claim 12, further including repeating step (a) pursuant to a prescribed schedule so that in the presence of a changing natural conduction time, preemptive ventricular pacing continues to trigger the mechanical contraction sequence that improves cardiac output.

14. The method of claim 12, wherein step (b) includes delivering the V-pulse to the prescribed ventricular location at a time in the cardiac cycle that is less than the natural conduction time by an amount Δ, where Δ is 1 to 100 msec.

15. The method of claim 14 wherein the step of determining the natural conduction time comprises measuring the natural conduction time for y consecutive cardiac cycles, where y is an integer, and computing an average of the natural conduction time interval measurements thus made.

16. A method of treating a patient's heart suffering from cardiomyopathy, comprising:

(a) monitoring a plurality of cardiac cycles of the patient's heart to determine a natural conduction time, where the natural conduction time commences with an atrial event and terminates with a natural ventricular event within a given cardiac cycle; and (b) applying an electrical stimulus to a prescribed ventricular location at a time, following an atrial event in each cardiac cycle, that is less than the natural conduction time determined in step (a), whereby the electrical stimulus preempts a natural ventricular event in the presence of a substantially constant natural conduction time, the electrical stimulus thus delivered triggering a mechanical contraction sequence that improves cardiac output.

17. The method of claim 16, further including applying the electrical stimulus to the prescribed ventricular location at a time in the cardiac cycle that is 1 to 100 msec before the termination of the natural conduction time, and hence 1 to 100 msec before a natural ventricular event occurs in the cardiac cycle.

18. The method of claim 17, further including applying the electrical stimulus to a ventricular location adapted to cause a mechanical contraction sequence of the heart that differs from a natural contraction sequence of the type that follows a natural ventricular event.

19. A dual-chamber pacemaker for controlling ventricular pacing in order to increase cardiac output in a patient suffering from cardiomyopathy by preemptively stimulating a ventricle of the patient's heart, comprising:

an atrial lead having an electrode in contact with one of the atria of the heart, and a ventricular lead having an electrode in contact with one of the ventricles of the heart;

means for sensing a natural conduction time interval of the patient through the electrodes of the atrial and ventricular leads, the natural conduction time interval comprising the time interval between atrial activity, whether sensed or paced, and a natural ventricular depolarization (R-wave);

pulse generator means for generating a ventricular stimulation pulse (V-pulse) upon the timing out of an AV time interval and applying the V-pulse to the electrode of the ventricular lead; and timing means, coupled to the pulse generator means, for defining the AV time interval to begin with atrial activity, and for setting the AV time interval to a value that, for ventricular pacing, is always less than the natural conduction time interval by a prescribed amount;

whereby the V-pulse is generated by the pulse generator means and applied to one of the ventricles of the heart prior to the occurrence of natural ventricular activity for preemptively stimulating the ventricle to thereby increase cardiac output.

20. A method of treating cardiomyopathy using an implanted dual-chamber pacemaker, the pacemaker including means for sensing atrial and ventricular events, means for generating a ventricular stimulation pulse (V-pulse), and means for delivering the V-pulse to an apex of the ventricle, said method comprising:

measuring a natural conduction time as the difference between an atrial event and a natural ventricular event within a given cardiac cycle; and generating and delivering the V-pulse to the ventricular apex at a time that is less than the measured natural conduction time;

whereby the V-pulse preempts a natural ventricular event, the V-pulse thereby triggering an apical mechanical contraction sequence that improves cardiac output.

* * * * *